(12) United States Patent
Fonnum et al.

(10) Patent No.: US 10,676,790 B2
(45) Date of Patent: *Jun. 9, 2020

(54) CONJUGATION OF CARBOXYL FUNCTIONAL HYDROPHILIC BEADS

(71) Applicants: LIFE TECHNOLOGIES CORPORATION, Carlsbad, CA (US); LIFE TECHNOLOGIES AS, Carlsbad, CA (US)

(72) Inventors: Geir Fonnum, Oslo (NO); Steven M. Menchen, Fremont, CA (US); Alfred Lui, Sunnyvale, CA (US); Guobing Xiang, Hayward, CA (US); Synne Larsen, Oslo (NO)

(73) Assignees: LIFE TECHNOLOGIES CORPORATION, Carlsbad, CA (US); LIFE TECHNOLOGIES AS, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 16/206,957

(22) Filed: Nov. 30, 2018

(65) Prior Publication Data

US 2019/0177787 A1 Jun. 13, 2019

Related U.S. Application Data

(63) Continuation of application No. 15/200,588, filed on Jul. 1, 2016, now Pat. No. 10,144,968.

(Continued)

(51) Int. Cl.
*C12Q 1/68* (2018.01)
*C12Q 1/6876* (2018.01)
(Continued)

(52) U.S. Cl.
CPC .............. *C12Q 1/6874* (2013.01); *C08J 7/14* (2013.01); *C12Q 1/6853* (2013.01);
(Continued)

(58) Field of Classification Search
CPC .. C12Q 1/6874; C12Q 1/6876; C12Q 1/6853; C08J 7/14; C08J 2333/26
See application file for complete search history.

(56) References Cited

U.S. PATENT DOCUMENTS 4,451,613 A 5/1984 Rousseau et al.
4,507,382 A 3/1985 Rousseau et al.
(Continued)

FOREIGN PATENT DOCUMENTS

EP 0512844 11/1992
EP 1726661 11/2006
(Continued)

OTHER PUBLICATIONS

Wilchek et al., Improved Method for Preparing N-Hydroxysuccinimide Ester-Containing Polymers for Affinity Chromatography Bioconjugate Chem. 1994, 5 491-492.*
(Continued)

*Primary Examiner* — Robert D Harlan

(57) ABSTRACT

A polymer substrate, such as a polymer coating or a polymer hydrogel network, includes carboxyl moieties that can be used as conjugation sites to which receptor or analyte molecules can be attached. In an example, the polymer substrate includes a polyacrylamide polymer network having alkanoic acid moieties or derivatives thereof, which can react with carboxyl activating compounds to provide an activated alkanoate moieties on the polyacrylamide network. Amine-terminated nucleic acids can react with the activated alkanoate moieties to capture the nucleic acid to the polymer network through an alkylamide moiety.

20 Claims, 7 Drawing Sheets

Related U.S. Application Data

(60) Provisional application No. 62/188,382, filed on Jul. 2, 2015.

(51) Int. Cl.
*C12Q 1/6874* (2018.01)
*C12Q 1/6869* (2018.01)
*C08J 7/14* (2006.01)
*C12Q 1/6853* (2018.01)

(52) U.S. Cl.
CPC ......... *C12Q 1/6869* (2013.01); *C12Q 1/6876* (2013.01); *C08J 2333/26* (2013.01)

(56) References Cited

U.S. PATENT DOCUMENTS

| | | | |
|---|---|---|---|
| 4,507,497 | A | 3/1985 | Reilly et al. |
| 5,281,698 | A | 1/1994 | Nitecki |
| 5,387,510 | A | 2/1995 | Wu |
| 5,512,439 | A | 4/1996 | Hornes et al. |
| 5,677,373 | A | 10/1997 | Berge et al. |
| 6,242,235 | B1 | 6/2001 | Schultz et al. |
| 6,525,183 | B2 | 2/2003 | Vinayak et al. |
| 7,217,762 | B1 | 5/2007 | Joergedal et al. |
| 7,534,621 | B2 | 5/2009 | Okada |
| 9,139,667 | B2 | 9/2015 | Menchen et al. |
| 9,243,085 | B2 | 1/2016 | Fonnum et al. |
| 9,938,577 | B2 | 4/2018 | Fonnum et al. |
| 10,144,968 | B2 * | 12/2018 | Fonnum ............... C12Q 1/6876 |
| 10,150,992 | B2 | 12/2018 | Menchen et al. |
| 2004/0014080 | A1 | 1/2004 | Tanga et al. |
| 2004/0203040 | A1 | 10/2004 | Okada |
| 2004/0215011 | A1 | 10/2004 | Deggerdal et al. |
| 2005/0014001 | A1 | 1/2005 | Fonnum et al. |
| 2006/0131542 | A1 | 6/2006 | Weng et al. |
| 2007/0299249 | A1 | 12/2007 | Songe et al. |
| 2008/0139399 | A1 | 6/2008 | Fonnum et al. |
| 2009/0026082 | A1 | 1/2009 | Rothberg et al. |
| 2009/0069554 | A1 | 3/2009 | Finne et al. |
| 2009/0081371 | A1 | 3/2009 | Minami et al. |
| 2009/0291506 | A1 | 11/2009 | Fonnum et al. |
| 2010/0137143 | A1 | 6/2010 | Rothberg et al. |
| 2010/0207051 | A1 | 8/2010 | Fonnum et al. |
| 2010/0282617 | A1 | 11/2010 | Rothberg et al. |
| 2010/0304982 | A1 | 12/2010 | Hinz et al. |
| 2013/0210991 | A1 | 8/2013 | Fonnum et al. |

FOREIGN PATENT DOCUMENTS

| | | | |
|---|---|---|---|
| EP | 2224014 | | 9/2010 |
| JP | H05211899 | | 8/1993 |
| JP | 2002211954 | | 7/2002 |
| JP | 2004258026 | | 9/2004 |
| JP | 2007003439 | | 1/2007 |
| JP | 2007508416 | | 4/2007 |
| JP | 2009092651 | | 4/2009 |
| JP | 2009516008 | | 4/2009 |
| WO | WO-2002000600 | | 1/2002 |
| WO | WO-2002072791 | | 9/2002 |
| WO | WO-2003084982 | | 10/2003 |
| WO | WO-2003091392 | | 11/2003 |
| WO | WO-2004086046 | | 10/2004 |
| WO | WO-2005017180 | | 2/2005 |
| WO | WO-2005037902 | | 4/2005 |
| WO | WO-2005074993 | | 8/2005 |
| WO | WO-2006103094 | | 10/2006 |
| WO | WO-2006125124 | | 11/2006 |
| WO | WO-2007020041 | | 2/2007 |
| WO | WO-2007040986 | | 4/2007 |
| WO | WO-2008005675 | | 1/2008 |
| WO | WO-2010125170 | | 11/2010 |
| WO | WO-2011053940 | | 5/2011 |
| WO | WO 2013/119936 A2 * | 8/2013 | ............... C08F 2/16 |
| WO | WO-2013119894 | | 8/2013 |
| WO | WO-2013119936 | | 8/2013 |
| WO | WO-2013119956 | | 8/2013 |
| WO | WO-2017004559 | | 1/2017 |
| WO | WO-2017007774 | | 1/2017 |

OTHER PUBLICATIONS

Devor et al., "Strategies for Attaching Oligonucleotides to Solid Supports", Integrated DNA Technologies 2005, 2010, and 2011, US, Jan. 1, 2005, URL:https://www.idtdna.comjpagesjdocsjdefault-sourcejtechnical-reportsjstrategies-for-attaching-oligonucleotides-to v6-3-14-14.pdf?sfvrsn=2 [retrieved on Aug. 9, 2016].

Dong et al., "Effect of Secondary Structure on the Activity of Enzymes Suspended in Organic Solvents", *Archives of Biochemistry and Biophysics*, vol. 334, No. 2, Article No. 0472, 1996, 406-414.

EP17160771, Search Report, dated Sep. 14, 2017, 1-20.

EP17160771, Partial Search Report, dated Jul. 3, 2017, 1-19.

Ghosh et al., "N, N'-disuccinimidyl carbonate: a useful reagent for alkoxycarbonylation of amines", Tetrahedron Letters, vol. 33, No. 20, May 12, 1992, 2781-2784.

Haginaka et al., "Separation of enantiomers on a chiral stationary phase based on ovoglycoprotein—I. Influences of the pore size of base silica materials and bound protein amounts on chiral resolution", Journal of Chromatography A, vol. 773, Nos. 1-2, Jun. 27, 85-91.

Ion Torrent Systems, "GO Club (Genaris Omics Club)", http://genaport.genaris.com/GOC_sequencer_post.php?eid=00006, 2010, 1-2.

Lee, "Solubility of Tetrabutylammonium Bromide in Benzene between 298.15 K and 323.15 K", *Journal of Chemical & Engineering Data*, vol. 47, No. 5, 2002, 1135-1139.

Li et al., "Enzyme-linked synthetic oligonucleotide probes: non-radioactive detection of enterotoxigenic *Escherichia coli* in faecal specimens", *Nucleic Acids Research*, vol. 15, No. 13, Jul. 10, 1987, 5275-5287.

Ling et al., "Polymer-bound cellulose phenylcarbamate derivatives as chiral stationary phases for enantioselective HPLC", *Journal of Separation Science*, vol. 26, 2003, 1337-1346.

Meyer et al., "Hydrophobic Ion Pairing: Altering the Solubility Properties of Biomolecules", *Pharmaceutical Research*, vol. 15, No. 2, 1998, 188-193.

Murakami et al, Hybrid Hydrogels to Which Single-Stranded (ss) DNA Probe Is Incorporated Can Recognize Specific ssDNA, 2005, *Macromolecules*, vol. 38, 2005, 1535-1537.

Nemat-Gorgani et al., "The Interaction of Phospholipid Membranes and Detergents with Glutamate Dehydrogenase", *European Journal of Biochemistry*, vol. 74, No. 1, Mar. 1977, 129-137.

Nimse et al: "Immobilization Techniques for Microarray: Challenges and Applications", *Sensors*, vol. 14, No. 12, Nov. 25, 2014, 22208-22229.

Ogura, et al., "A Novel Active Ester Synthesis Reagent", *Tetrahedron Letters*, vol. 49, Jan. 1, 1979, 4745-4746.

PCT/US2013/025352, International Preliminary Report on Patentability, dated Aug. 12, 2014, 1-11.

PCT/US2013/025352, International Search Report and Written Opinion, dated May 22, 2013, 1-18.

PCT/US2016/040767, International Preliminary Report on Patentability, dated Jan. 11, 2018, 1-9.

PCT/US2016/040767, International Search Report and Written Opinion, dated Oct. 11, 2016, 1-14.

PCT/US2016/041012, International Search Report and Written Opinion, dated Oct. 4, 2016, 2017, 1-10.

PCT/US2016/041012, International Preliminary Report on Patentability, dated Jan. 9, 2018, 1-6.

Peppas et al., "Hydrogels in Biology and Medicine: From Molecular Principles to Bionanotechnology", *Advanced Materials*, vol. 18, 2006, 1345-1360.

Poellmann et al., "Characterizing and Patterning Polyacrylamide Substrates Functionalized with N-Hydroxysuccinimide", *Cellular and Molecular Bioengineering*, vol. 6, No. 3, Sep. 2013, 299-309.

(56) References Cited

OTHER PUBLICATIONS

Powers et al., "Enhanced Solubility of Proteins and Peptides in Nonpolar Solvents Through Hydrophobic Ion Pairing", *Biopolymers*, vol. 33, No. 6, 1993, 927-932.

Tang et al., "Polymerizing immobilization of acrylamide-modified nucleic acids and its application", *Biosensors and Bioelectronics*, vol. 24, No. 7, Mar. 15, 2009, 1817-1824.

Wang et al., "Different EDC/NHS activation mechanisms between PAA and PMAA brushes and the following amidation reactions", *Langmuir: The ACS Journal of Surfaces and Colloids*, vol. 27, No. 19, Oct. 4, 2011, 12058-12068.

Wilchek et al., "improved method for preparing n-hydroxysuccinimide ester-containing polymers for affinity chromatography", *Bioconiuciate Chemistry*, vol. 5, No. 5, Jan. 1, 1994, 491-492.

Xion et al, "Responsive ONA-Based Hydrogels and Their Applications", *Macromolecular Rapid Communications*, vol. 34, No. 16, Jul. 16, 2013, 1271-1283.

\* cited by examiner

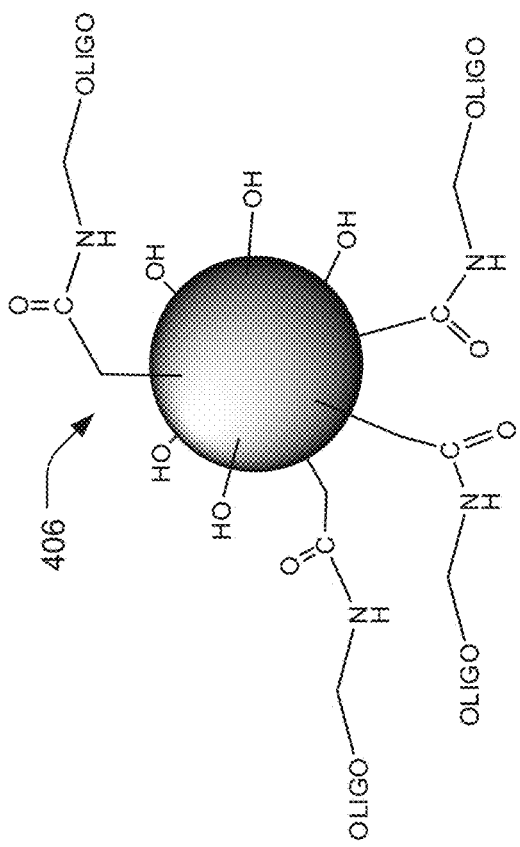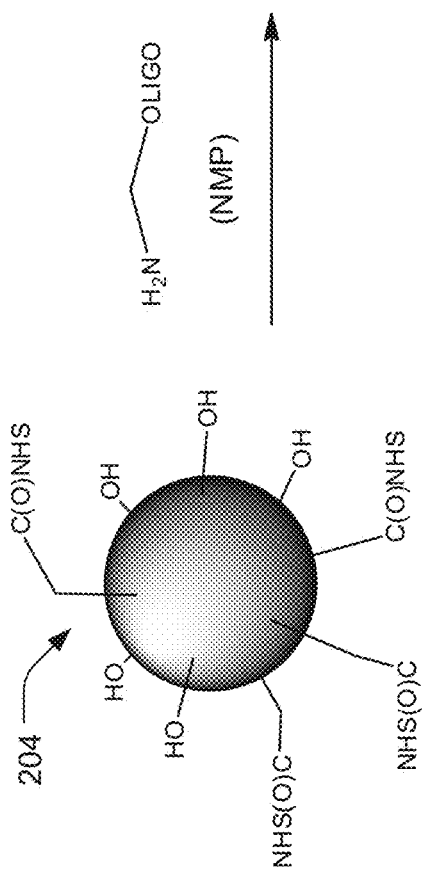
FIG. 4

CONJUGATION OF CARBOXYL FUNCTIONAL HYDROPHILIC BEADS

CROSS-REFERENCE TO RELATED APPLICATION(S)

This application is a continuation of U.S. application Ser. No. 15/200,588 filed Jul. 1, 2016, which claims benefit of U.S. Provisional Application No. 62/188,382, filed Jul. 2, 2015. The entire contents of the aforementioned applications are incorporated by reference herein.

FIELD OF THE DISCLOSURE

This disclosure, in general, relates to methods for conjugating carboxyl functional hydrophilic beads and beads formed by such methods.

BACKGROUND

Functionalized polymer substrates are finding use in various chemical and biological applications. In particular, polymer coatings on surfaces and polymer beads can be used in various separation techniques or to assist with detecting analytes in both chemical and biological systems. For example, polymeric particles have been used in chromatographic techniques to separate target molecules from a solution. In another example, polymeric particles having a magnetic coating are utilized in magnetic separation techniques. More recently, polymeric particles have been used to enhance ELISA-type techniques and can be used to capture polynucleotides.

Such separation and analytical techniques depend on functionalizing the polymer substrate to attract the desired analyte. Previous substrates have suffered from poor surface functionalization or difficulty in controlling the number of functionalized sites. Poor functionalization can lead to a reduction in analyte capture or expression of captured analytes, either through a lack of sites, poor access to sites, or other steric hindrances. For magnetic separations techniques, variance in analyte capture can lead to low efficiency separations. For chromatographic techniques and various polynucleotide capture techniques, variance in functionalization can lead to variance in the number of sites available for interacting with polynucleotides, leading to variance in capture or separation efficiency or detection.

SUMMARY

In an exemplary embodiment, a polymer substrate, such as a polymer coating, a polymer hydrogel network, or a polymer bead, includes carboxyl moieties that can be used as conjugation sites to which receptor or analyte molecules can be attached. In a particular example, the polymer substrate includes a polyacrylamide polymer network having alkanoic acid moieties or derivatives thereof, which can react in a non-aqueous solvent with carboxylate activating compounds, such as a succinimidyl uronium compound or a succinimidyl phosphonium compound, to provide activated alkanoate moieties, such as succinimidyl esters, on the polyacrylamide network. Lipophilic, amine-terminated nucleic acids, such as amine-terminated oligonucleotides, can react with the activated alkanoate moieties in non-aqueous solvents to capture the nucleic acid to the polymer network through an alkylamide moiety.

BRIEF DESCRIPTION OF THE DRAWINGS

The present disclosure may be better understood, and its numerous features and advantages made apparent to those skilled in the art by referencing the accompanying drawings.

FIG. 2, FIG. 3, FIG. 4, FIG. 5 and FIG. 6 include illustrations of exemplary chemical schemes.

The use of the same reference symbols in different drawings indicates similar or identical items.

DETAILED DESCRIPTION

Figure 1:
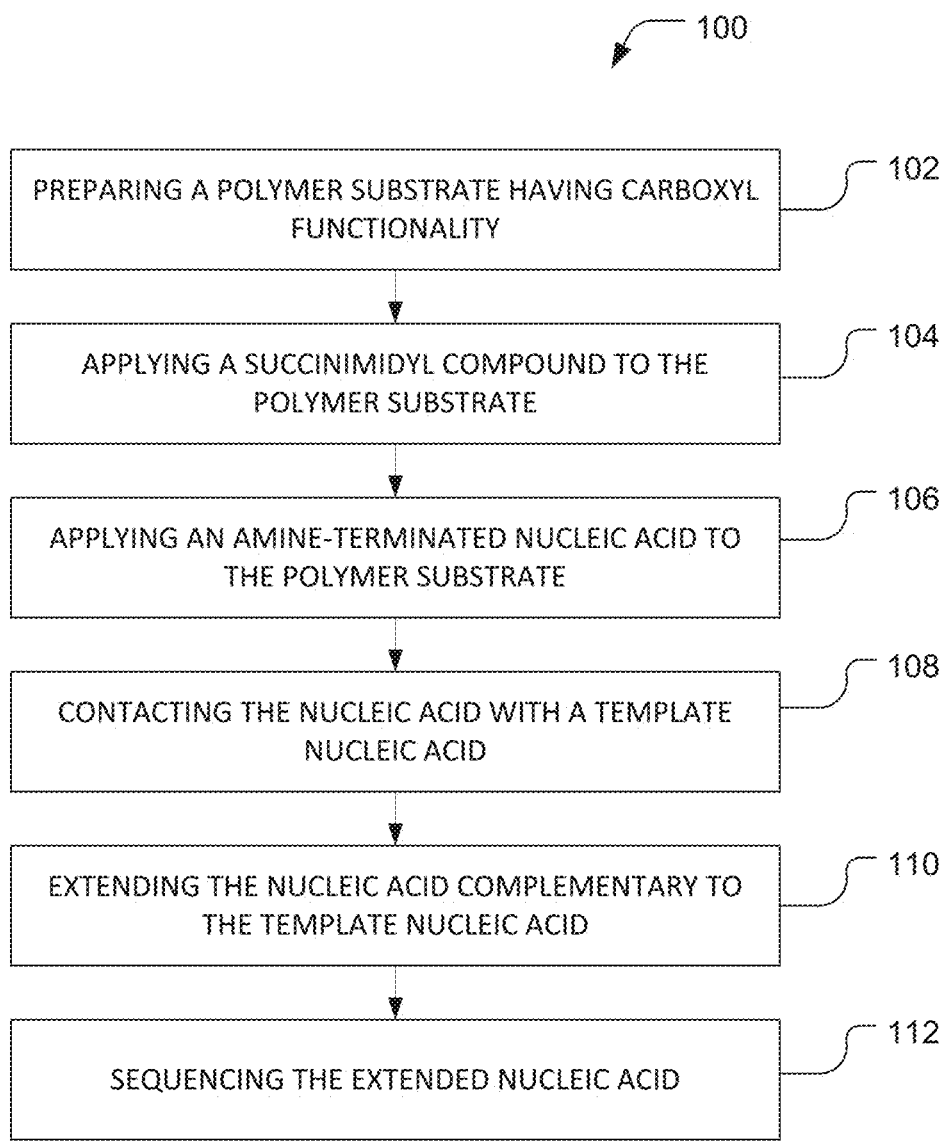
FIG. 1 includes a block flow diagram illustrating an exemplary method for conjugating a substrate and a detecting an analyte.

In an exemplary embodiment, a polymer substrate, such as a polymer coating, a polymer hydrogel network, or a discrete polymer particle, includes carboxyl moieties that can be used as conjugation sites to which receptor or analyte molecules can be attached. In a particular example, the polymer substrate includes a polyacrylamide polymer network having alkanoic acid moieties or ester derivative thereof, which can react in a non-aqueous solvent with carboxyl activating compounds, such as a succinimidyl uronium compound or a succinimidyl phosphonium compound, to provide activated alkanoate moieties on the polyacrylamide network. Lipophilic amine-terminated nucleic acids, such as amine-terminated oligonucleotides, can react in a non-aqueous solvent with the succinimidyl alkanoate moieties to capture the nucleic acid to the polymer network through an alkylamide moiety.

For example, a coating, bead, or hydrogel substrate can be formed of a polyacrylamide polymer network that is functionalized with an alkanoic acid moiety or an ester derivative thereof. In particular, the polyacrylamide polymer network can be formed from copolymerization of acrylamide monomers having carboxyl moieties or ester derivatives thereof and acrylamide monomers or crosslinkers having hydroxyl moieties. The ratio of the carboxyl functional monomer to the acrylamide monomer and crosslinker including hydroxyl moieties influences the availability of conjugation sites that are reactive to carboxyl activating compounds, such as succinimidyl uronium salts or succinimidyl phosphonium salts. Alternatively, carboxy functional polymer acrylamide substrates can be formed by hydrolyzing a polyacrylamide substrate, for example, using an acid treatment. When conjugated with ion-exchanged or lipophilic amine-terminated biomolecules in non-aqueous solvents, such as an amine-terminated nucleic acid (e.g., an amine-terminated oligonucleotide), the polymeric coating, hydrogel network, or bead can include a polyacrylamide polymer network having alkylamide moieties directly linked to nitrogen of the amide moiety on the acrylamide backbone of the polyacrylamide network and linked to the biomolecule, such as the nucleic acid.

In an exemplary embodiment, a polymer substrate, for example, in a non-aqueous solvent, can be formed by applying a succinimidyl compound to the polymer of the substrate. The polymer substrate can include an alkanoic acid moiety or ester derivative thereof, which is reactive with the succinimidyl compound to form a succinimidyl alkanoate moiety. An ion-exchanged or liphophilic amine-terminated biomolecule, such as an amine-terminated nucleic acid for which cationic counter ions have been exchanged to comprise oil soluble ammonium or phosphonium cations, can be applied in a non-aqueous solvent over the substrate with the amine functionality of the amine-terminated biomolecules forming an amide in place of the succinimidyl group and leaving an alkylamide moiety coupling the polymer backbone to the biomolecules.

In an example, FIG. 1 illustrates a method 100 for conjugating a substrate. As illustrated at 102, a polymer substrate having carboxyl functionality is prepared. The polymer substrate can be a coating. In another example, the polymer substrate can be a polymer particle. For example, the polymer particle can be a hydrophilic polymer particle, such as a hydrogel polymer particle.

Figure 2:
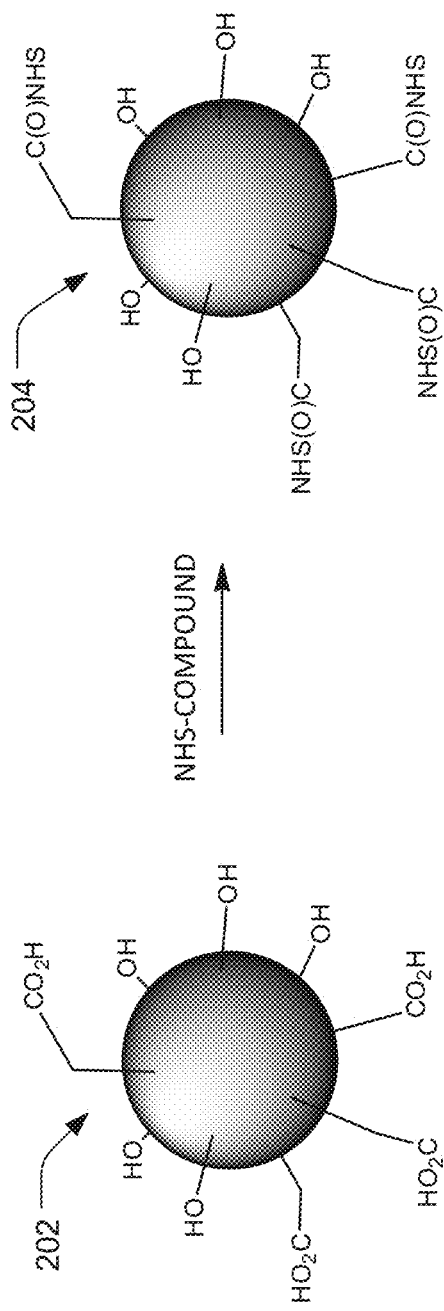

For example, as illustrated in FIG. 2, a polymer particle 202 can include moieties terminating in carboxyl functionality. For example, carboxyl functionality can result from alkanoic acid moieties or ester derivatives thereof extending from a backbone of the polymer of the polymer particle. Optionally, the polymer particle 202 can also express other functionalities, such as hydroxyl functionalities or amine functionalities. While the polymer particle 202 is illustrated as having the moieties and functionalities expressed at a surface of the polymer particle 202, the moieties and functionality can extend throughout the polymer particle 202 including interior to the polymer particle 202. In particular, functionality internal to the polymer particle 202 can be accessed and conjugated.

In an example, the polymer particle can be formed by polymerizing a mixture of one or more monomers or crosslinkers. The monomer can include a carboxyl functional acrylamide monomer. Depending on the polymerization method, the carboxyl functional acrylamide monomer includes a protected carboxyl functional acrylamide monomer. In particular, the protected carboxyl functional acrylamide includes a protection group protecting the hydrophilic OH of the carboxyl functionality, preventing reaction during polymerization or rendering the monomer more miscible with hydrophobic phases.

For example, the monomer can have the formula (I):

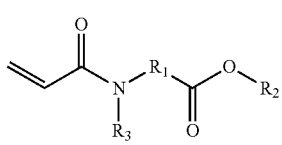

wherein $R_1$ is an alkyl group having between 3 and 10 carbons, is a polyether group having between 1 and 10 ether units, or is another polar group, wherein $R_2$ is a linear or branched alkyl group having between 3 and 8 carbons or is a silyl group, and wherein $R_3$ is hydrogen or an alkyl group having between 1 and 6 carbons. In a particular example, $R_1$ is an alkyl group having between 3 and 10 carbons or is a polyether group having between 1 and 10 ether units For example, $R_1$ can be an alkyl group having 3 to 6 carbons, such as 3 to 5 carbons. In another example, $R_1$ can be a polyether group including units, such as including ethylene oxide or propylene oxide units, in a range of 2 to 6 units, such as 2 to 4 units. In a further example, $R_1$ can be a polar group, for example, including a secondary amine. In an example, $R_2$ is a branched alkyl group, for example, having 3 to 5 carbons, such as 4 carbons. In particular, $R_2$ can be an isopropyl, isobutyl, sec-butyl, or tert-butyl group, or any combination thereof. The silyl group can be a trialkyl silyl group, an organo disilyl group, or an organo trisilyl group. For example, the trialkyl silyl group can be a trimethyl silyl or a triethyl silyl group. In a further example, $R_3$ is hydrogen. In another example, $R_3$ is a methyl or ethyl group.

In an example, the monomer can have the formula (II):

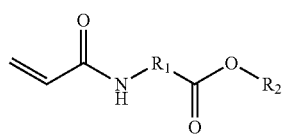

wherein $R_1$ is an alkyl group having between 3 and 10 carbons or is a polyether group having between 1 and 10 ether units, and wherein $R_2$ is a linear or branched alkyl group having between 3 and 8 carbons or is a silyl group. For example, $R_1$ can be an alkyl group having 3 to 6 carbons, such as 3 to 5 carbons. In another example, $R_1$ can be a polyether group including units, such as including ethylene oxide or propylene oxide units, in a range of 2 to 6 units, such as 2 to 4 units. In an example, $R_2$ is a branched alkyl group, for example, having 3 to 5 carbons, such as 4 carbons. In particular, $R_2$ can be an isopropyl, isobutyl, sec-butyl, or tert-butyl group, or any combination thereof. The silyl group can be a trialkyl silyl group, an organo disilyl group, or an organo trisilyl group. For example, the trialkyl silyl group can be a trimethyl silyl or a triethyl silyl group.

In a particular example, the protected carboxy functional monomer can be acrylamidobutanoate protected with a tert-butyl protection group and having the formula (III):

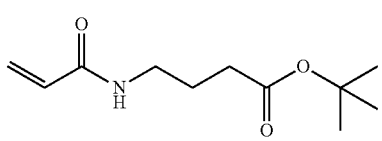

In addition to the protected carboxy functional monomer, one or more comonomers or crosslinkers can polymerize with the caboxyl functional monomer. The comonomer or crosslinker can be a radically polymerizable comonomer or crosslinker, such as a vinyl-based comonomer or crosslinker. Depending on the method of polymerization, the comonomer or crosslinker can include a hydrophilic monomer coupled to a hydrophobic protection group. In an example, the hydrophilic comonomer can include acrylamide, vinyl acetate, or any combination thereof. In a particular example, the comonomer is an acrylamide, such as an acrylamide including hydroxyl groups, carboxyl groups, or a combination thereof. In another example, the acrylamide comonomer can be a hydroxyalkyl acrylamide, such as hydroxyethyl acrylamide. In particular, the hydroxyalkyl acrylamide can include N-(hydroxymethyl)acrylamide (IV, illustrated below), N-(hydroxyethyl)acrylamide (V, illustrated below), or a combination thereof.

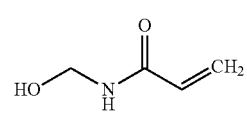

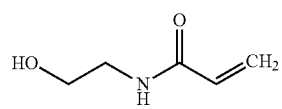

In a particular example, the hydrophilic comonomer or crosslinker include hydroxyl groups. In a further example, a mixture of the carboxyl functional monomer and a comonomer or crosslinker, such as a mixture of carboxyl functional acrylamide monomer and hydroxyalky acrylamide comonomer can be used. In an example, the carboxyl functional acrylamide monomer can be included in a ratio relative to hydroxyalkyl acrylamide in a range of 2:1 to 1:1000, such as a range of 2:1 to 1:100, a range of 1:1 to 1:25, a range of 1:1 to 1:10 or even a range of 1:1 to 1:2.

A crosslinker can also be polymerized with the monomers. In an example, the crosslinker is included in a mass ratio of monomers to crosslinker in a range of 15:1 to 1:2, such as a range of 10:1 to 1:1, a range of 6:1 to 1:1, or even a range of 4:1 to 1:1. The crosslinker can have a low water solubility (e.g., less than 10 g/l) or can have protected polar group, resulting in a preference for a hydrophobic phase. Protected polar groups can be deprotected following polymerization to render the crosslinker functionality hydrophilic. In particular, the crosslinker can be a divinyl crosslinker. For example, a divinyl crosslinker can include a diacrylamide, such as N,N'-(ethane-1,2-diyl)bis(2-hydroxyl ethyl)acrylamide, N,N'-(2-hydroxypropane-1,3-diyl)diacrylamide, or a combination thereof. In another example, a divinyl crosslinker includes ethyleneglycol dimethacrylate, divinylbenzene, hexamethylene bisacrylamide, trimethylolpropane trimethacrylate, a protected derivative thereof, or a combination thereof. In a further example, the crosslinker can be protected with a hydrophobic protection group, such as a hydroxyl protection group.

In addition, the polymerization can occur in the presence of a porogen. An exemplary porogen includes an aromatic porogen. In an example, the aromatic porogen includes benzene, toluene, xylene, mesitylene, phenethylacetate, diethyladipate, hexylacetate, ethylbenzoate, phenylacetate, butylacetate, or a combination thereof. The porogen typically has a Solubility parameter of 15-20. In another example, the porogen is an alkanol porogen, such as dodecanol. The porogen can be included in amounts relative to the polymerizing phase within the reactive system in a range of 1 wt % to 99 wt %, such as a range of 30 wt % to 90 wt % or even a range of 50 wt % to 85 wt %.

Optionally, a polymerization initiator can be included. An exemplary polymerization initiator can initiate polymerization through free radical generation. An exemplary polymerization initiator includes an azo initiator, such as oil soluble azo initiators. Another initiator can include ammonium persulfate. A further exemplary initiator can include tetramethylethylenediamine. In an example, the polymerization initiator can be included in an amount of 0.001 wt % to 3 wt % based on the weight of the polymerization phase.

Alternatively, the polymer particle can be formed by hydrolyzing a polyacrylamide formed from the polymerization of hydroxyl alkyl acrylamide and a crosslinker A portion of the hydroxyl alkyl amide units are converted to carboxyl functionality in response to an acid treatment.

Returning to FIG. 1, a carboxyl activating compound, such as a succinimidyl compound, can be applied to the polymer substrate, as illustrated at 104, for example in a non-aqueous solvent. The succinimidyl compound can react with the carboxyl functionality, such as an alkanoic acid moiety or ester derivative thereof, to form a succinimidyl alkanoate moiety, referred to herein as activation.

A succinimidyl compound can be applied to the polymer substrate. The succinimidyl compound, for example, can be a succinimidyl uronium compound or a succinimidyl phosphonium compound. In a particular example, the succinimidyl compound is a succinimidyl uronium compound. The succinimidyl uronium compound can be an O-type succinimidyl uronium. In an example, the O-type succinimidyl uronium is an N-hydroxy succinimidyl uronium. In another example, the succinimidyl compound is a succinimidyl phosphonium compound.

For example, as illustrated in FIG. 2, an N-hydroxy succinimidyl compound (NHS-compound) can react with the carboxyl functionality on the particle 202, for example, in a non-aqueous solvent, to form the succinimidyl alkanoate compound (C(O)NHS) illustrated on particle 204.

Returning to FIG. 1, the modified polymer substrate can be conjugated to a biomolecule, such as a nucleic acid, by applying an amine-terminated biomolecule, for example, dissolved in a non-aqueous solvent, to the polymer substrate, as illustrated at 106. In a particular example, the biomolecule can be made lipophilic by exchanging metal counter ions with cations, such as ammonium or phosphonium cations, having lipohpillic moieties. In a particular example, an amine-terminated nucleic acid can undergo ion exchange prior to conjugation with the polymer substrate. In particular, metal ions associated with the nucleic acid can be replaced with lipophilic counter ions, as illustrated in FIG. 3.

Figure 3:
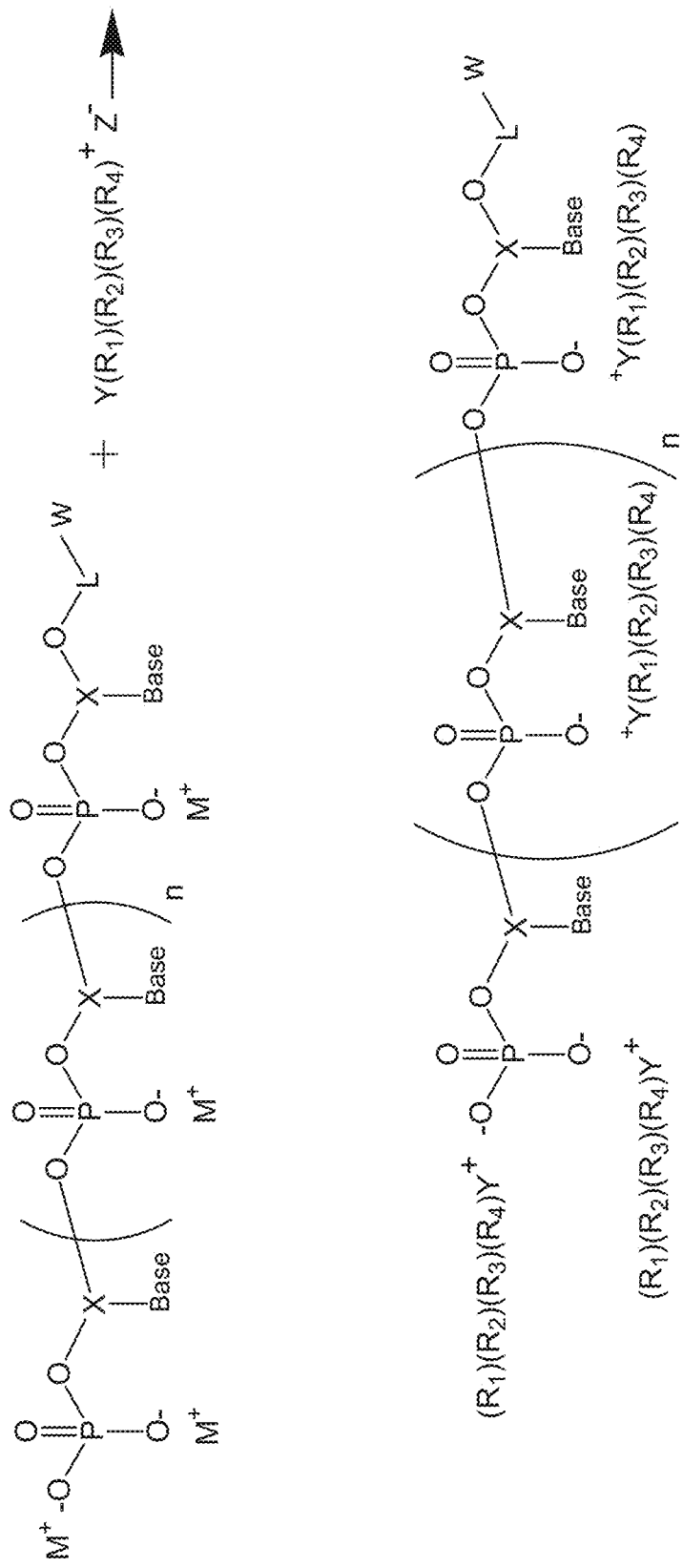

As illustrated in FIG. 3, counter ions (e.g., metal ions) of a biomolecule can be exchanged with lipophilic counter ions to provide a biomolecule complex that is more lipophilic. As used herein, lipophilic counter ions are ions that incorporate functionality (e.g., alkyl moieties) that, when the counter ion is associated with the biomolecule, shield ions of the biomolecule, rendering the biomolecule more lipophilic and able to dissolve in a non-aqueous solvent. For example, the illustrated biomolecule is a polynucleotide. As illustrated, the polynucleotide is formed of a plurality of polymerized nucleotides. The carbohydrate moiety (X) of a nucleotide is bound to a phosphate group of a neighboring nucleotide. Each phosphate group is associated with a cationic counter ion ($M^+$). In an example, the cationic counter ion ($M^+$) can be a metal ion. In another example, the cationic counter ion ($M^+$) can be ammonium or proton. In addition, the polynucleotide can include a linker group (L), linking a reactive group (W) to the nucleotide chain. Alternatively, the biomolecule can be a polynucleotide analog having a similar linker/reactive group structure, and the polynucleotide can have the reactive group (W) extending off one or more of the bases in addition to or instead of off the carbohydrate (X).

In an example, the linker group (L) includes a hydrocarbon, an ether or polyether group, or a combination thereof. The reactive group (W) can function to react with functional groups formed on a substrate, such as a polymeric substrate. In a particular example, the reactive group (W) can be an amine, thiol, maleimide, acetylene, azide, or a combination thereof. For example, the reactive group (W) can be an amine or a thiol. In particular, the reactive group (W) can be an amine. In another example, the reactive group (W) can be a maleimide. In a further example, the reactive group (W) can be acetylene. In an additional example, the reactive group (W) can be an azide.

In the example illustrated in FIG. 3, the polynucleotide is exposed to a lipophilic counter ion, such as a positively-charged counter ion having liphophilic moieties. The lipophilic counter ion can include a positively-charged member (Y) coupled to one or more hydrocarbon groups (R1, R2, R3, R4) and associated with an opposing ion (Z). In an example, the positively charged member (Y) can be nitrogen, phosphorus, sulfur, arsenic, or any combination thereof. In particular, the positively charged member (Y) is nitrogen, phosphorous, sulfur, or a combination thereof. For example, the positively charged member (Y) can be a nitrogen or phosphorous. In particular, the positively charged member (Y) is nitrogen, forming an amine with hydrocarbon groups (R1, R2, R3, or R4).

The positively charged member (Y) can be coupled to one or more hydrocarbon groups, such as at least two hydrocarbon groups, at least three hydrocarbon groups, or at least four hydrocarbon groups, but generally not greater than five hydrocarbon groups. As illustrated, the positively charged member (Y) includes four hydrocarbon groups (R1, R2, R3, or R4). The hydrocarbon groups (R1, R2, R3, or R4) independently can be an alkyl group, an aryl group, ether derivatives thereof, or combinations thereof. In an example, an alkyl hydrocarbon group can include a methyl, ethyl, propyl, or butyl group, an ether derivative thereof, or a combination thereof. For example, the propyl can be an n-propyl, an iso-propyl, or a combination thereof. In an example, the butyl group can be an n-butyl, isobutyl, sec-butyl, tert-butyl, or any combination thereof. An exemplary aryl group can include a phenyl, tolyl, xylyl, or poly-aryl, such as naphthyl, ether derivatives thereof, or any combination thereof.

In particular, the lipophilic counter ion [Y(R1)(R2)(R3)(R4)] can include a lipophilic ammonium ion, a lipophilic phosphonium ion, a lipophilic arsonium ion, a lipophilic sulfonium ion, or a combination thereof. An exemplary lipophilic ammonium ion includes a tetraalkylammonium, a tetraarylammonium, mixed alkyl and aryl ammonium, or a combination thereof. For example, an exemplary lipophilic ammonium ion is selected from the group consisting of tetramethylammonium, tetraethylammonium, tetrapropylammonium, tetrabutylammonium, tetrapentylammonium, tetrahexylammonium, tetraheptylammonium, tetraoctylammonium, alkyl and aryl mixtures thereof, or a combination thereof. An exemplary lipophilic phosphonium ion includes tetraphenylphosphonium. An exemplary lipophilic arsonium ion is a tetraalkylarsonium, a tetraarylarsonium, a mixed alkyl and aryl arsonium ion, or a combination thereof. For example, the lipophilic arsonium ion is tetraphenylarsonium. An exemplary lipophilic sulfonium ion is a trialkylsulfonium ion. The ion (Z) can be an ion of opposite charge to the lipophilic group [Y(R1)(R2)(R3)(R4)], such as a hydroxide, a halogen, a nitrate, a carbonate, a sulfate, a perchlorate, a phenolate, a tetraalkylborate, a tetraarylborate, a phosphate ion, or any combination thereof.

As a result of the exchange, the polynucleotide complex exhibits lipophilic behavior and can be dispersed in a nonaqueous solvent. In an example, the nonaqueous solvent is polar. In a further example, the nonaqueous solvent is not reactive with coupling groups on the substrate or functional groups of the polymer, such as the reactive group (W) of the polynucleotide complex. In an example, the solvent includes an amide, a urea, a carbonate, an ether, a sulfoxide, a sulfone, a hindered alcohol, or a combination thereof. An exemplary amide or urea includes formamide, N,N-dimethylformamide, acetamide, N,N-dimethylacetamide, hexamethylphosphoramide, pyrrolidone, N-methylpyrrolidone, N,N,N',N'-tetramethylurea, N,N'-dimethyl-N,N'-trimethyleneurea, or a combination thereof. An exemplary carbonate includes dimethyl carbonate, propylene carbonate, or a combination thereof. An exemplary ether includes tetrahydrofuran. An exemplary sulfoxide or sulfone includes dimethylsulfoxide, dimethylsulfone, or a combination thereof. An exemplary hindered alcohol includes tert-butyl alcohol. In a particular example, the solvent includes N-methylpyrrolidone.

Following the exchange or as part of the exchange, the polynucleotide complex can be dispersed in the nonaqueous solvent. The dispersed polynucleotide complex can be used for conjugation of a substrate.

For example, as illustrated in FIG. 4, succinimidyl alkanoate moieties of the polymer particle 204 when reacted with an amine-terminated nucleic acid, such as an amine-terminated oligonucleotide, particularly in a nonaqueous solution, such as those described above, can react to form a particle 406 in which the nucleic acid is attached to the polymer substrate and the polymer backbone of the polymer substrate through an amide group.

Figure 5:
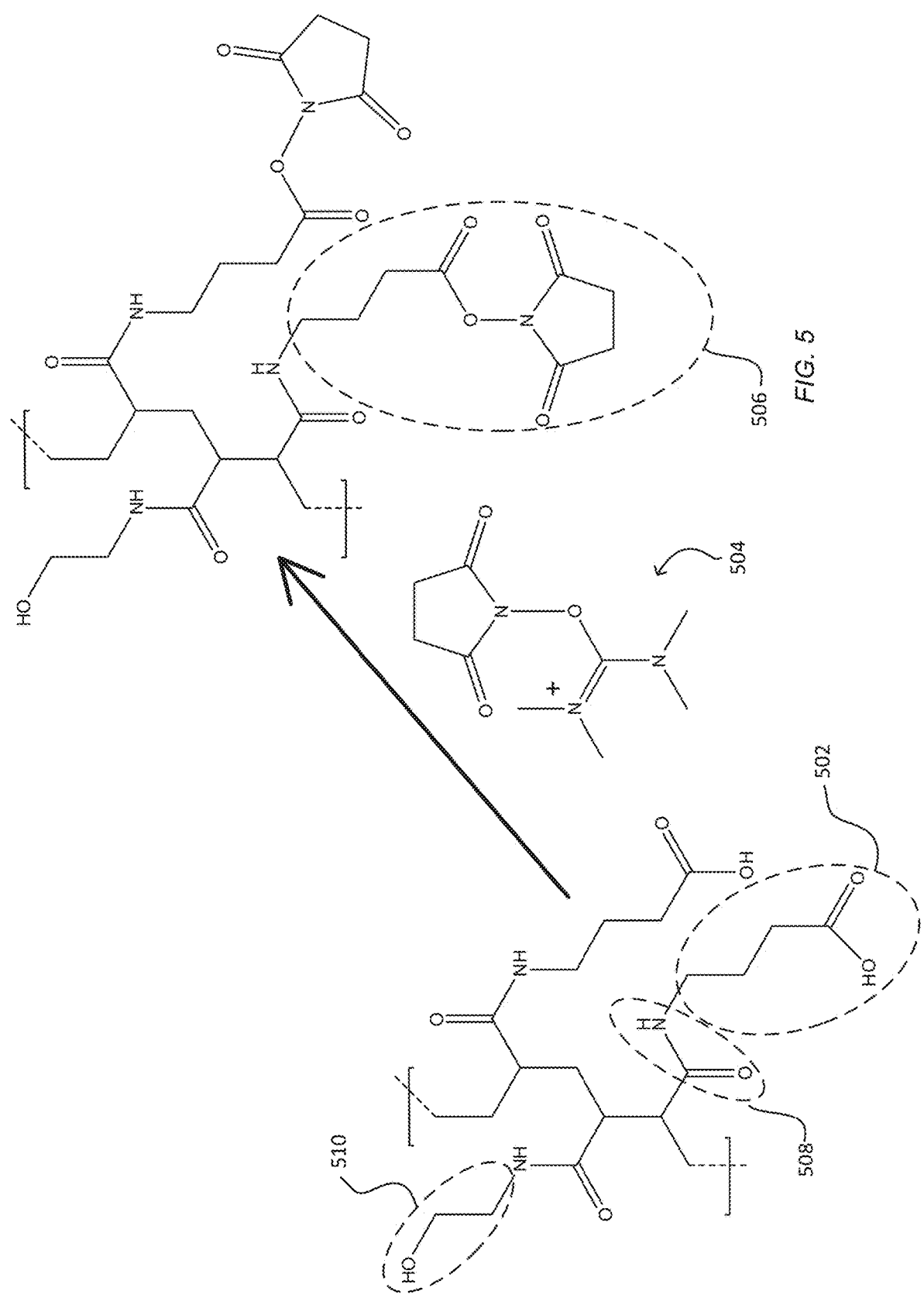

In a particular example illustrated in FIG. 5, a polyacrylamide polymer network can include moieties directly attached to the nitrogen of the amide group 508 of the polyacrylamide polymer network. For example, an alkanoic acid moiety 502 or ester derivative thereof can be directly attached to the nitrogen of the amide 508. In an example, the alkanoic acid moiety 502 can have 3 to 10 carbons, such as 3 to 8 carbons, 3 to 6 carbons, or 3 to 5 carbons. Optionally, other moieties can be attached to other amide groups of the polyacrylamide network. For example, a hydroxyl moiety 510 can be attached to the polymer network.

Figure 6:
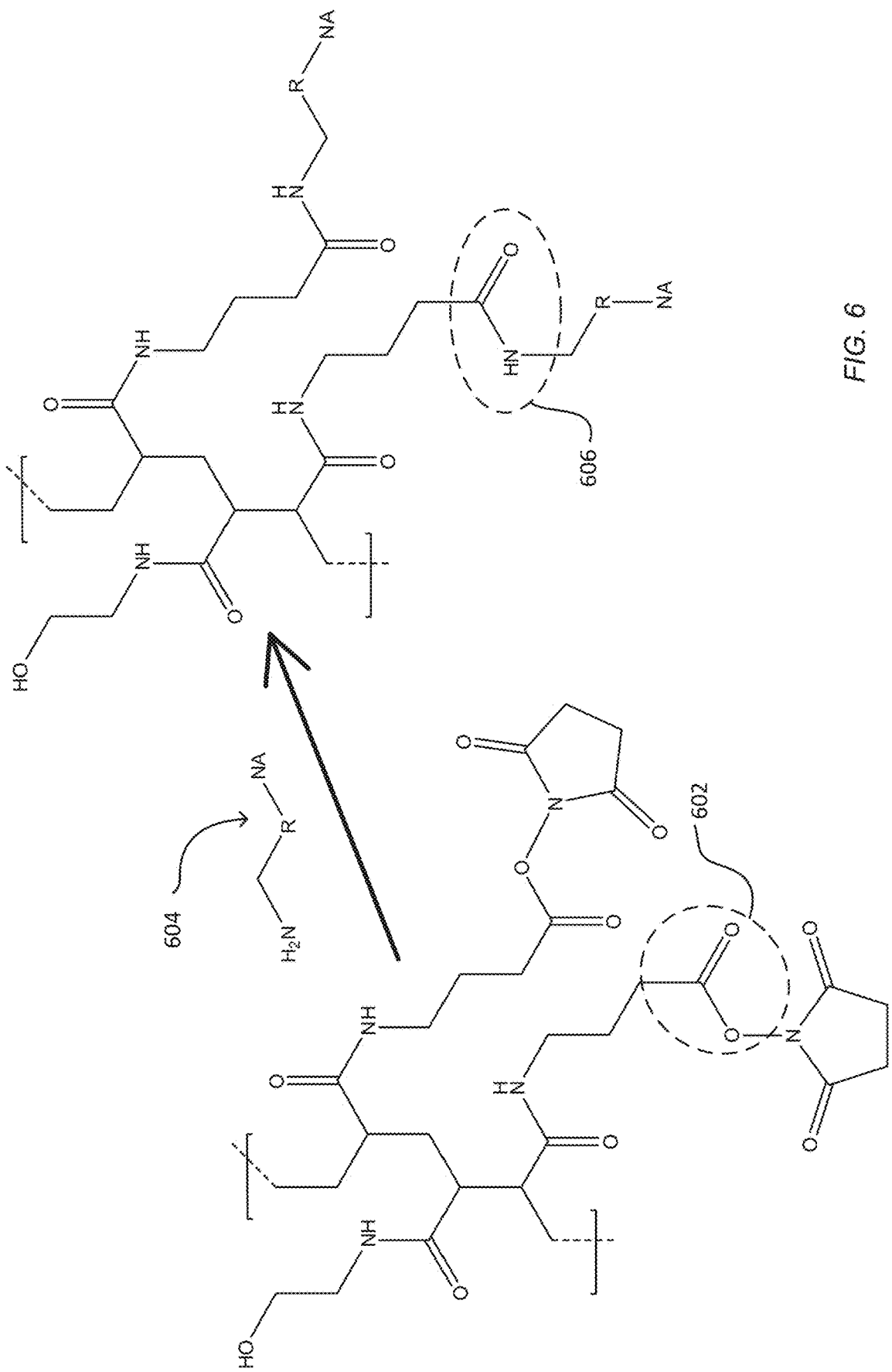

To facilitate conjugation of the biomolecule, a succinimidyl compound, such as an N-hydroxy succinimidyl uronium 504 can react with the alkanoic acid moiety 502, for example, in a non-aqueous solvent, to form a succinimidyl alkanoate moiety 506. As illustrated in FIG. 6, the resulting succinimidyl alkanoate moiety 506 can be reacted with a lipophilic amine-terminated nucleic acid in a non-aqueous solvent to conjugate the nucleic acid to the polyacrylamide backbone. In particular, the succinimidyl group can be removed from the succinimidyl alkanoate moiety 506, converting the ester group 602 to an amide group 606 and coupling the amine-terminated nucleic acid 604 to the polyacrylamide backbone. The amine-terminated nucleic acid 604 can include a nucleic acid (NA) coupled to the amine ($H_2N-$) through a moiety (R). In an example, R is an alkyl group, an ether group, or any combination thereof. In a particular example, the amine-termination can be at a 5' end of the nucleic acid. In particular, the conjugation can preferentially be performed in a non-aqueous solution.

In the case of a polymer substrate that includes a polymer hydrogel network, the polymer hydrogel network can include a polyacrylamide polymer network having the alkyl amide moiety directly coupled to the nitrogen of the amide of the acrylamide polymer network and also coupled to the nucleic acid through the functional group (R), which can be an alkyl group or polyether group. In particular, the alkyl group can have 3 to 8 carbons.

In such a manner, the polymer substrate originally having carboxyl functionality can be conjugated to a biomolecule, such as a nucleic acid. In a particular example, the nucleic acid can be an oligonucleotide primer complementary to a portion of a template nucleic acid. In methods involving the capture of template nucleic acids, amplification of such templates, or testing, such as sequencing, of the nucleic acids, the nucleic acid template can be contacted with the nucleic acid conjugated to the polymer substrate, as illustrated at 108. In particular, the nucleic acid conjugated to the polymer substrate can be an oligonucleotide primer complementary to a 3' end portion of a template nucleic acid. In an alternative example, the oligonucleotide primer conjugated to the polymer substrate can be complementary to the 5' end portion of the template nucleic acid or can be complementary to an intermediate portion of the template nucleic acid.

Particularly in sequencing applications, the oligonucleotide primer can be extended complementary to the template nucleic acid, as illustrated at 110. For example, the oligonucleotide can act as a primer, which, when associated with the template nucleic acid and exposed to enzymes and nucleotides under the appropriate conditions, can extend complementary to the template nucleic acid, forming a complementary copy of the template nucleic acid. Optionally, the template nucleic acid can be separated from the extended oligonucleotide primer and can attach to other complementary oligonucleotide primers conjugated to the polymer substrate. Such other oligonucleotide primers can be extended, creating multiple complementary copies of the template nucleic acid conjugated to the polymer substrate.

As illustrated at 112, the extended nucleic acid or oligonucleotide primer can be sequenced, as described below. Alternatively, the conjugated particles can be used in separation techniques. For example, the conjugated particles can be used to capture target polynucleotides. In an example, the polynucleotides conjugated to the polymer can be extended based on captured target polynucleotides. Such conjugated particles can be used in sequencing techniques, such as an ion-based or pH-based sequencing techniques.

Figure 7:
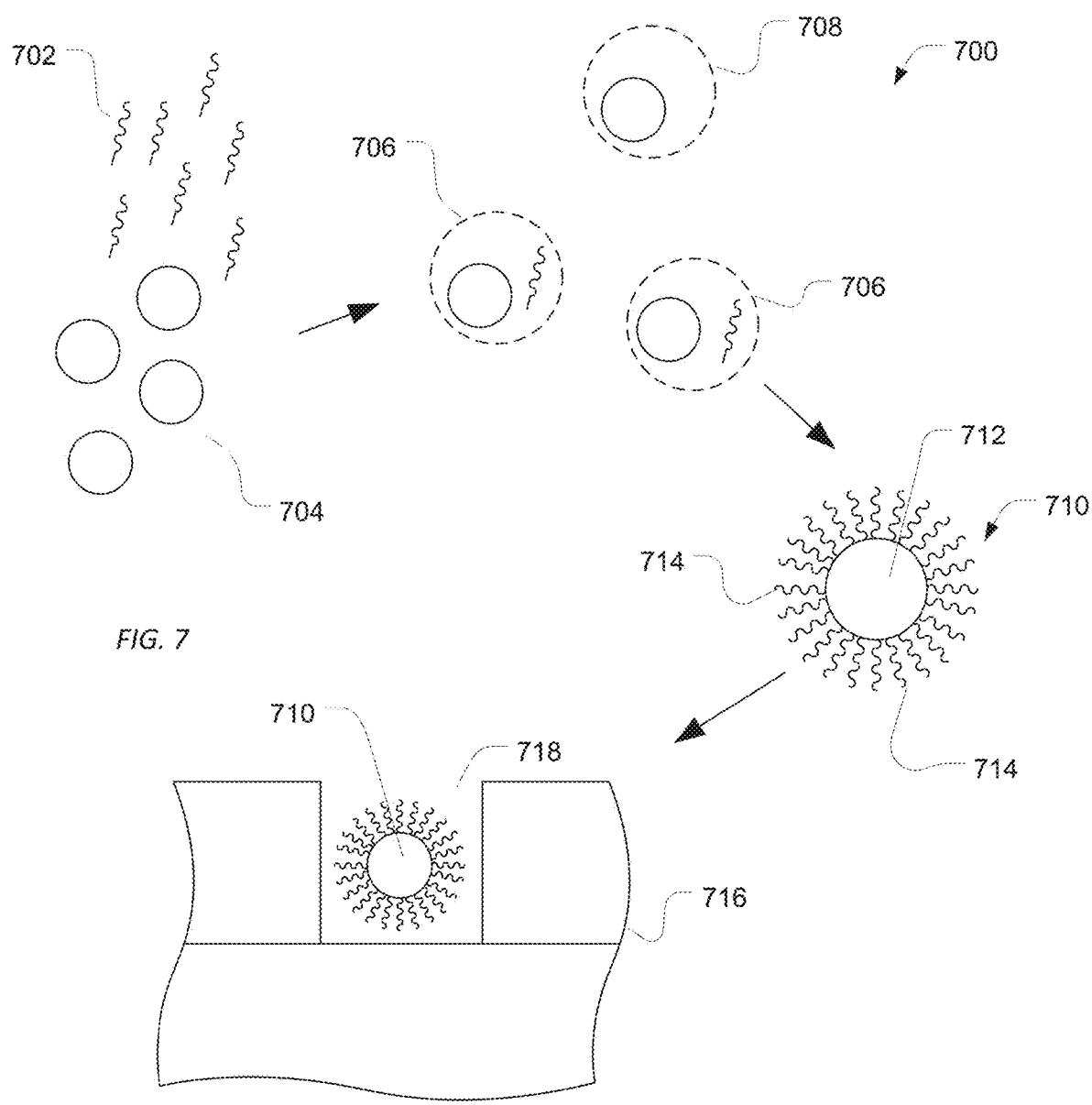
FIG. 7 includes a diagram of an exemplary sequencing method.

For example, as illustrated in FIG. 7, a plurality of conjugated polymeric particles 704 can be placed in a solution along with a plurality of target polynucleotides 702. The plurality of particles 704 can be conjugated with probe polynucleotides to bind with target polynucleotides 702. For example, the conjugated particles 704 can include an oligonucleotide complementary to a portion of the target polynucleotides 702.

In a particular embodiment, the particles 704 and polynucleotides 702 are subjected to polymerase chain reaction (PCR) amplification. For example, dispersed phase droplets 706 or 708 are formed as part of an emulsion and can include a hydrophilic hydrogel particle or a polynucleotide. In an example, the target polynucleotides 702 and the hydrophilic particles 704 are provided in low concentrations and ratios relative to each other such that a single polynucleotide 702 is likely to reside within the same dispersed phase droplets as a single hydrophilic particle 704. Other droplets, such as a droplet 708, can include a single hydrophilic particle and no polynucleotide. Each droplet 706 or 708 can include enzymes, nucleotides, salts or other components sufficient to facilitate duplication of the polynucleotide. Alternatively, amplification techniques, such as recombinase polymerase amplification (RPA) with or without emulsion, can be used.

Duplication of the target polynucleotide can include modulating the duplication conditions. Modulating can optionally include: increasing or decreasing the polymerase concentration; increasing or decreasing the nucleotide concentration; increasing or decreasing a cation concentration; increasing or decreasing a reaction temperature, time or pH, and the like. Modulating can include increasing or decreasing the rate of the reaction, increasing or decreasing the yield of product of the reaction, and the like. Duplication can be performed in the presence of appropriate buffers or nucleotides (including nucleotide analogs or biotinylated nucleotides).

In particular, the polynucleotide to be amplified can be captured by the polymeric particle. Exemplary methods for capturing nucleic acid can include: hybridizing a polynucleotide to an oligonucleotide that is attached to a polymeric particle. Methods for capturing nucleic acids can include: (a) providing a polymeric particle attached to a single-stranded oligonucleotide (e.g., a capture oligonucleotide); (b) providing a single-stranded polynucleotide; and (c) hybridizing the single-stranded oligonucleotide to the single-stranded polynucleotides, thereby capturing the single-stranded polynucleotide to the polymeric particle. Each of the polymeric particles can be attached with a plurality of single-stranded oligonucleotides (e.g., capture oligonucleotides). In some embodiments, step (c) can be conducted with a plurality of single-stranded polynucleotides. In some embodiments, at least a portion of the single-stranded oligonucleotide includes a nucleotide sequence that is complementary (or partially complementary) to at least a portion of the single-stranded polynucleotide.

In an example, the method can further include amplifying the polynucleotide into a plurality of polynucleotides and attaching at least a portion of the plurality of polynucleotides to the hydrophilic particle, thereby generating a hydrophilic particle including a plurality of attached polynucleotides. Alternatively, the method can include amplifying the polynucleotide into a plurality of complementary polynucleotides by extending the conjugated oligonucleotide, thereby generating a hydrogel particle including a plurality of attached polynucleotides.

In additional examples, methods for nucleic acid amplification comprise: conducting a primer extension reaction on a polynucleotide that is hybridized to an oligonucleotide which is attached to a polymeric particle. In some embodiments, methods for nucleic acid amplification comprise: (a) providing a polymeric particle attached to a single-stranded oligonucleotide (e.g., a primer oligonucleotide); (b) providing a single-stranded template polynucleotide; (c) hybridizing the single-stranded oligonucleotide to the single-stranded template polynucleotide; (d) contacting the single-stranded template polynucleotide with a polymerase and at least one nucleotide under conditions suitable for the polymerase to catalyze polymerization of at least one nucleotide onto the single-stranded oligonucleotide so as to generate an extended single-stranded oligonucleotide. In some embodiments, the method further comprises: (e) removing (e.g., denaturing) the single-stranded template polynucleotide from the extended single-stranded oligonucleotide so that the single-stranded oligonucleotide remains attached to the polymeric particle; (f) hybridizing the remaining single-stranded oligonucleotide to a second single-stranded template polynucleotide; and (g) contacting the second single-stranded template polynucleotide with a second polymerase and a second at least one nucleotide, under conditions suitable for the second polymerase to catalyze polymerization of the second at least one nucleotide onto the single-stranded oligonucleotide so as to generate a subsequent extended single-stranded oligonucleotide. In some embodiments, steps (e), (f) and (g) can be repeated at least once. In some embodiments, the polymerase and the second polymerase comprise a thermostable polymerase. In some embodiments, the conditions suitable for nucleotide polymerization include conducting the nucleotide polymerization steps (e.g., steps (d) or (g)) at an elevated temperature. In some embodiments, the conditions suitable for nucleotide polymerization include conducting the nucleotide polymerization step (e.g., steps (d) or (g)) at alternating temperatures (e.g., an elevated temperature and a relatively lower temperature). In some embodiments, the alternating temperature ranges from 60-95° C. In some embodiments, the temperature cycles can be about 10 seconds to about 5 minutes, or about 10 minutes, or about 15 minutes, or longer. In some embodiments, methods for nucleic acid amplification can generate one or more polymeric particles each attached to a plurality of template polynucleotides comprising sequences that are complementary to the single-stranded template polynucleotide or to the second single-stranded template polynucleotide. In some embodiments, each of the polymeric particles can be attached with a plurality of single-stranded oligonucleotides (e.g., capture oligonucleotides). In some embodiments, step (b), (c), (d), (e), (f) or (g) can be conducted with a plurality of single-stranded polynucleotides. In some embodiments, at least a portion of the single-stranded oligonucleotide comprises a nucleotide sequence that is complementary (or partially complementary) to at least a portion of the single-stranded polynucleotide. In some embodiments, methods for nucleic acid amplification (as described above) can be conducted in an aqueous phase solution in an oil phase (e.g., dispersed phase droplet).

Following PCR, particles are formed, such as particle 710, which can include the hydrophilic particle 712 and a plurality of copies 714 of the target polynucleotide or complements thereof. While the polynucleotides 714 are illustrated as being on a surface of the particle 710, the polynucleotides 714 can extend within the particle 710. Hydrogel and hydrophilic particles having a low concentration of polymer relative to water can include polynucleotide segments on the interior of and throughout the particle 710 or polynucleotides can reside in pores and other openings. In particular, the particle 710 can permit diffusion of enzymes, nucleotides, primers and reaction products used to monitor the reaction. A high number of polynucleotides per particle produces a better signal in particular sequencing techniques.

In an exemplary embodiment, the particle 710 can be utilized in a sequencing device. For example, a sequencing device 716 can include an array of wells 718. A particle 710 can be placed within a well 718.

In an example, a primer can be added to the wells 718 or the particle 710 can be pre-exposed to the primer prior to placement in the well 718. The primer and polynucleotide form a nucleic acid duplex including the polynucleotide (e.g., a template nucleic acid) hybridized to the primer. The nucleic acid duplex is an at least partially double-stranded polynucleotide. Enzymes and nucleotides can be provided to the well 718 to facilitate detectible reactions, such as nucleotide incorporation.

Sequencing can be performed by detecting nucleotide addition. Nucleotide addition can be detected using methods such as fluorescent emission methods or ion detection methods. For example, a set of fluorescently labeled nucleotides can be provided to the system 716 and can migrate to the well 718. Excitation energy can be also provided to the well 718. When a nucleotide is captured by a polymerase and added to the end of an extending primer, a label of the nucleotide can fluoresce, indicating which type of nucleotide is added.

In an alternative example, solutions including a single type of nucleotide can be fed sequentially. In response to nucleotide addition, the pH within the local environment of the well 718 can change. Such a change in pH can be detected by ion sensitive field effect transistors (ISFET). As such, a change in pH can be used to generate a signal indicating the order of nucleotides complementary to the polynucleotide 714 of the particle 710.

In particular, a sequencing system can include a well, or a plurality of wells, disposed over a sensor pad of an ionic sensor, such as a field effect transistor (FET). In some embodiments, a system includes one or more polymeric particles loaded into a well which is disposed over a sensor pad of an ionic sensor (e.g., FET), or one or more polymeric particles loaded into a plurality of wells which are disposed over sensor pads of ionic sensors (e.g., FET). In some embodiments, an FET can be a chemFET or an ISFET. A "chemFET" or chemical field-effect transistor, includes a type of field effect transistor that acts as a chemical sensor. It is the structural analog of a MOSFET transistor, where the charge on the gate electrode is applied by a chemical process. An "ISFET" or ion-sensitive field-effect transistor can be used for measuring ion concentrations in solution; when the ion concentration (such as H+) changes, the current through the transistor changes accordingly.

The FET may be a FET array. As used herein, an "array" is a planar arrangement of elements such as sensors or wells. The array may be one or two dimensional. A one dimensional array can be an array having one column (or row) of elements in the first dimension and a plurality of rows (or columns) in the second dimension. The number of columns (or rows) in the first and second dimensions may or may not be the same.

One or more microfluidic structures can be fabricated above the FET sensor array to provide for containment or confinement of a biological or chemical reaction. For example, in one implementation, the microfluidic structure(s) can be configured as one or more wells (or microwells, or reaction chambers, or reaction wells, as the terms are used interchangeably herein) disposed above one or more sensors of the array, such that the one or more sensors over which a given well is disposed detect and measure analyte presence, level, or concentration in the given well. In some embodiments, there can be a 1:1 correspondence of FET sensors and reaction wells.

Returning to FIG. 7, in another example, a well 718 of the array of wells can be operatively connected to measuring devices. For example, for fluorescent emission methods, a well 718 can be operatively coupled to a light detection device. In the case of ionic detection, the lower surface of the well 718 may be disposed over a sensor pad of an ionic sensor, such as a field effect transistor.

Exemplary systems involving sequencing via detection of ionic byproducts of nucleotide incorporation are the Ion Torrent PGM™, Proton™ or SS™ sequencers (Life Technologies), which are ion-based sequencing systems that sequences nucleic acid templates by detecting hydrogen ions produced as a byproduct of nucleotide incorporation. Typically, hydrogen ions are released as byproducts of nucleotide incorporations occurring during template-dependent nucleic acid synthesis by a polymerase. The Ion Torrent PGM™, Proton™ or SS™ sequencers detect the nucleotide incorporations by detecting the hydrogen ion byproducts of the nucleotide incorporations. The Ion Torrent PGM™, Proton™ or SS™ sequencers can include a plurality of template polynucleotides to be sequenced, each template disposed within a respective sequencing reaction well in an array. The wells of the array can each be coupled to at least one ion sensor that can detect the release of H+ ions or changes in solution pH produced as a byproduct of nucleotide incorporation. The ion sensor comprises a field effect transistor (FET) coupled to an ion-sensitive detection layer that can sense the presence of H+ ions or changes in solution pH. The ion sensor can provide output signals indicative of nucleotide incorporation which can be represented as voltage changes whose magnitude correlates with the H+ ion concentration in a respective well or reaction chamber. Different nucleotide types can be flowed serially into the reaction chamber, and can be incorporated by the polymerase into an extending primer (or polymerization site) in an order determined by the sequence of the template. Each nucleotide incorporation can be accompanied by the release of H+ ions in the reaction well, along with a concomitant change in the localized pH. The release of H+ ions can be registered by the FET of the sensor, which produces signals indicating the occurrence of the nucleotide incorporation. Nucleotides that are not incorporated during a particular nucleotide flow may not produce signals. The amplitude of the signals from the FET can also be correlated with the number of nucleotides of a particular type incorporated into the extending nucleic acid molecule thereby permitting homopolymer regions to be resolved. Thus, during a run of the sequencer multiple nucleotide flows into the reaction chamber along with incorporation monitoring across a multiplicity of wells or reaction chambers can permit the instrument to resolve the sequence of many nucleic acid templates simultaneously.

EXAMPLES

Example 1. Activation of a Carboxylate-Hydrogel

To a solution of 500 billion of carboxylate-hydrogel (hydrogel designation LR570; polymerization target diameter of 0.55 microns with monomer feed ratios of: 5.9% backbone monomer plus 1.8% cross-linker; 30 million carboxylate monomer/micron$^3$ of hydrogel polymerization volume), in 666 microliter of anhydrous, amine-free N-methylpyrrolidone (NMP), is added 6 mg of O—(N-Succinimidyl)-N,N,N',N'-tetramethyluronium tetrafluoroborate (TSTU), 12 microliters of tributylamine, and NMP to a final volume of 1.0 milliliter After shaking at room temperature for 1 hour, the suspension is centrifuged at 15,000 rpm for 0.5 hour. The supernatant is removed from the resulting pellet, and the pellet is re-suspended into 800 milliliters of fresh NMP and centrifuged for 1 hour at 15,000 rpm. The supernatant is removed from the NHS ester activated hydrogel comprising resulting pellet.

Example 2. Conjugation of the Hydrogel with Amine Terminal DNA Probe

An amount of 3.14 microliters of a 7.41 mM NMP solution of 5'-amine terminated 30-mer oligonucleotide (that has tetrabutylammonium counter ion for each oligonucleotide phosphate group) is added to the carboxylate NHS ester hydrogel pellet from Example 1. This suspension is diluted to 1500 microliter with NMP. After addition of 0.55 microliter of tributylamine, the reaction vessel is agitated in a thermomixer at 70° C. for 16 hours. Subsequently, the suspension is centrifuged at 15,000 rpm for 0.5 hour, and the supernatant is removed from the pellet. The pellet is re-suspended in 800 microliters of NMP and centrifuged for 0.5 hour at 15,000 rpm, and the supernatant is removed. The resulting pellet is re-suspended in 800 microliter of concentrated ammonium hydroxide (30%) and agitated for 15 minutes in a thermomixer at room temperature; 400 microliter of de-ionized water is added to the reaction mixture, which is then centrifuged for 0.5 hour at 15,000 rpm, followed by removal of the supernatant. The resulting pellet is re-suspended in 1.0 milliliter of aqueous 0.125N sodium hydroxide and agitated in a thermomixer for 15 min at room temperature, followed by centrifugation for 0.5 hour, and removal of the supernatant. The oligonucleotide conjugated hydrogel is purified by repeatedly re-suspending the pellets in 1.0 milliliter of distilled water, centrifuging for 0.5 hour at 15,000 rpm, removing the supernatant, and analyzing the pH of the supernatant; when the supernatant water washes reach a pH value of 7, purification is complete. At this point, the hydrogel pellet is re-suspended in 1.0 milliter of TE buffer (10 mM Tris, 1 mM EDTA brought to pH 8.0 with HCl) and heated at 80° C. for 1 hour; after centrifugation (0.5 hour at 15,000 rpm), the conjugated hydrogels are washed, as above, with 1.0 milliliter of de-ionized water. The resulting pellet is re-suspended in 1.75 milliliter of de-ionized water for later use. Analysis of the conjugated product for total oligonucleotide content with a cell sorter shows 200,000-300,000 oligonucleotide probes per hydrogel particle, with a particle size 0.61 micrometer.

Example 3. Activation of a Carboxylate-Hydrogel

To a solution of 75 billion of carboxylate-hydrogel (hydrogel designation LT597; diameter=1.2 microns with monomer feed ratios of: 7.0% backbone monomer plus cross-linker with 1.1% of the total being cross-linker; 4 million carboxylate monomer/micron$^3$ of hydrogel polymerization volume), in 7200 microliter of anhydrous, amine-free N-methylpyrrolidone (NMP), is added 22.6 mg of O—(N-Succinimidyl)-N,N,N',N'-tetramethyluroniumtetrafluoroborate (TSTU), 27 microliters of tributylamine, and NMP to a final volume of 7.5 milliliter After shaking at room temperature for 1 hour, the suspension is centrifuged at 15,000 rpm for 50 min. The supernatant is removed from the resulting pellet, and the pellet is re-suspended into 4 milliliters of fresh NMP and centrifuged for 1 hour at 15,000 rpm. The supernatant is removed from the NHS ester activated hydrogel comprising resulting pellet. Repeat the 4 ml NMP wash/spin one more time.

Example 4. Conjugation of the Hydrogel with Amine Terminal DNA Probe

An amount of 193.4 microliters of a 5.17 mM NMP solution of 5'-amine terminated 30-mer oligonucleotide (that has tetrabutylammonium counter ion for each oligonucleotide phosphate group) is added to the carboxylate NHS ester hydrogel pellet from Example 3. This suspension is diluted to 9.976 milliliter with NMP. After addition of 23.8 microliter of 42 mM tributylamine in NMP, total reaction volume of 10 ml, the reaction vessel is agitated in a thermomixer at 66° C. for 16 hours. To it is added 10 ml water and cooled to room temperature, and to this mixture is added 10 ml 0.25M NaOH. The mixture is agitated in a thermomixer for 15 min at room temperature and 1 milliliter 50×TE buffer solution is added, followed by centrifugation for 50 min, and removal of the supernatant. The resulting pellet is re-suspended in 10 milliliter of 1×TE, followed by centrifugation for 50 min, and removal of the supernatant. At this point, the hydrogel pellet is re-suspended in 10 milliliter of 1×TE buffer and heated at 80° C. for 1 hour; after centrifugation (50 min at 15,000 rpm) and removal of the supernatant, the conjugated hydrogels are washed, as above, with 10 milliliter of 1×TE, followed by centrifugation for 50 min, and removal of the supernatant. The resulting pellet is re-suspended in 14 milliliter of de-ionized water and filtered with 5 um syringe filter for later use. Analysis of the conjugated product for total oligonucleotide content shows 2,360,000 oligonucleotide probes per hydrogel particle, with a particle size 2.71 micrometer.

In a first aspect, a method of preparing a polymeric substrate includes in a non-aqueous solvent, contacting the polymer substrate with a carboxyl activating compound. The polymer substrate includes an alkanoic acid moiety or ester derivative thereof. The carboxyl activating compound and the alkanoic acid moiety react to form an activated alkanoate moiety. The method also includes contacting a liphophilic amine-terminated oligonucleotide and the polymer substrate in the non-aqueous solvent, the amine termination of the oligonucleotide forming an alkanamide moiety in place of the activated alkanoate moiety.

In an example of the first aspect, the polymer substrate includes polyacrylamide with the alkanoic acid moiety. For example, the polyacrylamide is a crosslinked polyacrylamide. In another example, the polyacrylamide further includes an alkanol moiety.

In another example of the first aspect and the above examples, the alkanoic acid moiety has 2 to 8 carbons. For example, the alkanoic acid moiety has 3 to 6 carbons.

In a further example of the first aspect and the above examples, the alkanoic acid moiety is appended to the acrylamide functionality by a polar moiety. For example, the polar moiety is a polyether structure. In an example, the polyether includes 1 to 10 ether units. In a further example, the ether units are derived from ethylene oxide or propylene oxide units.

In an additional example of the first aspect and the above examples, the polymer substrate is a polymer coating.

In another example of the first aspect and the above examples, the polymer substrate is a polymer hydrogel network.

In a further example of the first aspect and the above examples, the carboxylate activating compound is a succinimidyl compound.

In an additional example of the first aspect and the above examples, the succinimidyl compound includes a succinimidyl uronium compound, a succinimidyl phosphonium compound, or a combination thereof. For example, the succinimidyl compound is a succinimidyl uronium compound. In a particular example, the succinimidyl uronium is an O-type uronium compound.

In another example of the first aspect and the above examples, the method further includes contacting a template nucleic acid with the oligonucleotide, at least a portion of the template nucleic acid complementary to the oligonucleotide. For example, the method further includes extending the oligonucleotide complementary to the template nucleic acid.

In a further example of the first aspect and the above examples, the amine-terminated oligonucleotide includes the amine termination on a 5' end.

In an additional example of the first aspect and the above examples, the amine termination of the amine-terminated oligonucleotide includes an alkylamine termination moiety.

In a second aspect, a method of conjugating a polyacrylamide substrate includes, in a non-aqueous solvent, contacting the polyacrylamide substrate with a carboxyl activating compound. The polyacrylamide substrate includes a carboxyl moiety. The carboxyl activating compound and the carboxyl moiety react to form an activated alkanoate moiety. The method further includes, in the non-aqueous solvent, contacting a lipophilic amine-terminated nucleic acid and the polymer substrate, the amine termination of the nucleic acid forming an amide moiety in place of the activated alkanoate moiety.

In an example of the second aspect, the polyacrylamide further includes an alkanol moiety.

In another example of the second aspect and the above examples, the polyacrylamide substrate is a polyacrylamide coating.

In a further example of the second aspect and the above examples, the polyacrylamide substrate is a polyacrylamide hydrogel network.

In an additional example of the second aspect and the above examples, the carboxyl activating compound is a succinimidyl compound. For example, the succinimidyl compound includes a succinimidyl uronium compound, a succinimidyl phosphonium compound, or a combination thereof. In an example, the succinimidyl compound is a succinimidyl uronium compound. For example, the succinimidyl uronium is an O-type uronium compound.

In another example of the second aspect and the above examples, the method further includes contacting a template nucleic acid with the nucleic acid, at least a portion of the template nucleic acid complementary to the nucleic acid. For example, the method further includes extending the nucleic acid complementary to the template nucleic acid.

In a fourth aspect, a polymer hydrogel network is formed using the method of the above aspects and claims.

In a fifth aspect, a polymer bead includes a polyacrylamide polymer network having an alkanimide moiety directly coupled to a nitrogen moiety of the polyacrylamide polymer network and coupled to a nucleic acid.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method of conjugating a polyacrylamide substrate, the method comprising:

in a non-aqueous solvent, contacting the polyacrylamide substrate with a carboxyl activating compound, the polyacrylamide substrate including a carboxyl moiety, the carboxyl activating compound and the carboxyl moiety reacting to form an activated alkanoate moiety; and in the non-aqueous solvent, contacting a lipophilic amine-terminated nucleic acid and the polyacrylamide substrate, an amine termination moiety of the liphophilic amine-terminated nucleic acid forming an amide moiety in place of the activated alkanoate moiety.

2. The method of claim 1, wherein the polyacrylamide further includes an alkanol moiety.

3. The method of claim 1, wherein the polyacrylamide substrate is a polyacrylamide coating.

4. The method of claim 1, wherein the polyacrylamide substrate is a polyacrylamide hydrogel network.

5. The method of claim 1, wherein the carboxyl activating compound is a succinimidyl compound.

6. The method of claim 5, wherein the succinimidyl compound includes a succinimidyl uronium compound, a succinimidyl phosphonium compound, or a combination thereof.

7. The method of claim 6, wherein the succinimidyl compound is a succinimidyl uronium compound.

8. The method of claim 7, wherein the succinimidyl uronium is an O-type uronium compound.

9. The method of claim 1, further comprising contacting a template nucleic acid with the nucleic acid, at least a portion of the template nucleic acid complementary to the nucleic acid.

10. The method of claim 9, further comprising extending the nucleic acid complementary to the template nucleic acid.

11. The method of claim 10, further comprising amplifying to make a plurality of nucleic acids complementary to the template nucleic acid.

12. The method of claim 10, further comprising sequencing the extended nucleic acid.

13. The method of claim 12, further comprising sequencing with pH-based sequencing.

14. The method of claim 1, wherein the amine-terminated oligonucleotide includes the amine termination on a 5' end.

15. The method of claim 1, wherein the amine termination of the amine-terminated oligonucleotide includes an alkylamine termination moiety.

16. The method of claim 1, wherein the non-aqueous solvent is a polar solvent.

17. The method of claim 1, wherein the non-aqueous solvent is not reactive with the activated alkanoate moiety.

18. The method of claim 1, wherein the non-aqueous solvent is an amide, a urea, a carbonate, an ether, a sulfoxide, a sulfone, a hindered alcohol, or a combination thereof.

19. The method of claim 1, wherein the non-aqueous solvent is an amide or urea selected from formamide, N,N-dimethylformamide, acetamide, N,N-dimethylacetamide, hexamethylphosphoramide, pyrrolidone, N-methylpyrrolidone, N,N,N',N'-tetramethylurea, N,N'-dimethyl-N,N'-trimethyleneurea, or a combination thereof.

20. The method of claim 1, wherein the non-aqueous solvent is tetrahydrofuran.

\* \* \* \* \*